US005644063A

United States Patent [19]
Lindstrom et al.

[11] Patent Number: 5,644,063
[45] Date of Patent: Jul. 1, 1997

[54] IMIDAZO[4,5-C]PYRIDIN-4-AMINE INTERMEDIATES

[75] Inventors: Kyle J. Lindstrom, Houlton, Wis.; Nick Nikolaides, Woodbury, Minn.

[73] Assignee: Minnesota Mining and Manufacturing Company, St. Paul, Minn.

[21] Appl. No.: 455,285

[22] Filed: May 31, 1995

Related U.S. Application Data

[62] Division of Ser. No. 303,216, Sep. 8, 1994, Pat. No. 5,446,153.

[51] Int. Cl.$^6$ .................. C07D 213/62; C07D 213/70; C07D 213/72
[52] U.S. Cl. .................. 546/294; 546/296; 546/307
[58] Field of Search .................. 546/296, 294, 546/307

[56] References Cited

U.S. PATENT DOCUMENTS

| | | | |
|---|---|---|---|
| 3,899,508 | 8/1975 | Wikel | 548/374.1 |
| 4,689,338 | 8/1987 | Gerster | 514/293 |
| 4,698,348 | 10/1987 | Gerster | 514/293 |
| 4,929,624 | 5/1990 | Gerster et al. | 514/293 |
| 4,988,815 | 1/1991 | Andre et al. | 546/159 |
| 5,037,986 | 8/1991 | Gerster | 546/82 |
| 5,175,296 | 12/1992 | Gerster | 546/82 |
| 5,266,575 | 11/1993 | Gerster et al. | 514/293 |
| 5,268,376 | 12/1993 | Gerster | 514/293 |
| 5,346,905 | 9/1994 | Gerster | 514/293 |
| 5,352,784 | 10/1994 | Nikolaides et al. | 594/126 |
| 5,389,640 | 2/1995 | Gerster et al. | 514/293 |

FOREIGN PATENT DOCUMENTS

| | | |
|---|---|---|
| 90301766 | 9/1990 | European Pat. Off. . |
| 90304182 | 10/1990 | European Pat. Off. . |
| 0510260 A2 | 10/1992 | European Pat. Off. . |
| 91/06682 | 4/1992 | WIPO . |
| 92/01305 | 9/1992 | WIPO . |
| 92/07226 | 3/1993 | WIPO . |

OTHER PUBLICATIONS

J. Med. Chem., 1968, 11, 87, Jain et al.
J. Org. Chem., 1941, 6, 54, Tracy et al.
J. Chem. Soc., 1962, 3638, Davis et al.
Rec. Trav. Chim. 1944, 63, 231, Wibaut et al.
Recueil, 1961, 80, 545, Salemink.
J. Heterocyclic Chem., 1970, 7, 389, Wang.
J. Org. Chem., 1981, 46, 3040, Seeman et al.
J. Med. Chem., 1985, 28, 467, Houston et al.
Chemical Abstracts, vol. 61, No. 1, 6060G (1964) and its full text.
Tijdschr. Plantenziekten, vol. 68, 198–207 (1962).

Primary Examiner—Alan L. Rotman
Attorney, Agent, or Firm—Gary L. Griswold; Walter N. Kirn; Ted K. Ringsred

[57] ABSTRACT

Imidazo[4,5-c]pyridin-4-amines that induce interferon ($\alpha$) biosynthesis in human cells. Also disclosed are pharmaceutical compositions containing such compounds and methods of inducing interferon ($\alpha$) biosynthesis involving the use of such compounds.

3 Claims, No Drawings

IMIDAZO[4,5-C]PYRIDIN-4-AMINE INTERMEDIATES

This is a division of application Ser. No. 08/303,216 filed Sep. 8, 1994, now U.S. Pat. No. 5,446,153.

BACKGROUND OF THE INVENTION

1. Field of the Invention

This invention relates to imidazopyridine compounds and to intermediates in their preparation. In another aspect this invention relates to immunomodulator compounds and to antiviral compounds.

2. Description of the Related Art

Certain 1H-imidazo[4,5-c]quinolin-4-amines and methods for their preparation are known and disclosed, e.g., in U.S. Pat. Nos. 4,689,338, 5,037,985, and 5,175,296, EP-A 90.301766.3, PCT/US91/06682, PCT/US92/01305, and PCT/US92/07226 (Gerster), and U.S. Pat. No. 4,988,815 (Andre et al). Such compounds are said to have antiviral activity and certain of them are said to induce the biosynthesis of cytokines such as interferon. Certain 6'-C-alkyl-3-diazaneplanocin derivatives, some of which are imidazo[4,5-c]pyridin-4-amines, are known and disclosed in EP-A 0510260 A2 (Obara et al.). These compounds are said to have antiviral activity.

Further compounds having antiviral or immunomodulator activity may advance the fields of antiviral therapy and immunomodulator therapy.

SUMMARY OF THE INVENTION

This invention provides compounds of Formula I:

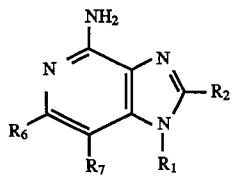

wherein $R_1$, $R_2$, $R_6$, and $R_7$ are defined below.

This invention also provides a pharmaceutical composition comprising a therapeutically effective amount of a compound of Formula I and a pharmaceutically acceptable vehicle.

This invention also provides a method of inducing interferon biosynthesis in an animal, comprising the step of administering to said animal a compound of Formula I in an amount effective to induce said interferon biosynthesis, and a method of treating a viral infection in an animal comprising the step of administering to said animal a compound of Formula I in an amount effective to inhibit the viral infection.

DETAILED DESCRIPTION OF THE INVENTION

The immunomodulator imidazo[4,5-c]pyridin-4-amines of this invention are compounds of the general Formula I:

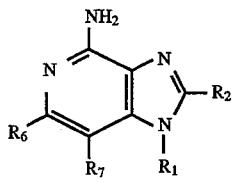

$R_1$ is selected from the group consisting of hydrogen; $CHR_xR_y$ wherein $R_x$ is hydrogen and $R_y$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and —CH═$CR_zR_z$ wherein each $R_z$ is independently straight chain, branched chain, or cyclic alkyl of one to about six carbon atoms.

Preferred $R_1$ substituents include 2-methylpropyl, n-butyl, 2-methyl-1-propenyl, ethoxyethyl, 2-hydroxy-2-methylpropyl, and 2-phenylethyl.

$R_2$ is selected from the group consisting of hydrogen, straight chain or branched chain alkyl containing one to about eight carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to about four carbon atoms.

When $R_2$ is alkyl it is preferably methyl, ethyl, propyl or butyl. When $R_2$ is hydroxyalkyl it is preferably hydroxymethyl. When $R_2$ is alkoxyalkyl, it is preferably ethoxymethyl.

$R_6$ and $R_7$ are independently selected from the group consisting of hydrogen and alkyl of one to about five carbon atoms, with the proviso that $R_6$ and $R_7$ taken together contain no more than six carbon atoms, and with the further proviso that when $R_7$ is hydrogen then $R_6$ is other than hydrogen and $R_2$ is other than hydrogen or morpholinoalkyl, and with the further proviso that when $R_6$ is hydrogen then $R_7$ and $R_2$ are other than hydrogen. Preferred $R_6$ and $R_7$ substituents include alkyl of one to about four carbon atoms, preferably methyl. Preferably both $R_6$ and $R_7$ are methyl.

Preferred compounds of the invention include:
2,7-dimethyl-1-(2-methylpropyl)-1H-imidazo[4,5-c]pyridin-4-amine;
2,6,7-trimethyl-1-(2-methylpropyl)-1H-imidazo[4,5-c]pyridin-4-amine;
4-amino-α,α,2,6,7-pentamethyl-1H-imidazo[4,5-c]pyridine-1-ethanol;
4-amino-2-butyl-α,α,6,7-tetramethyl-1H-imidazo[4,5-c]pyridine-1-ethanol;
4-amino-2-ethoxymethyl-α,α,6,7-tetramethyl-1H-imidazo[4,5-c]pyridine-1-ethanol;
1-(2-ethoxyethyl)-2,7-dimethyl-1H-imidazo[4,5-c]pyridin-4-amine;
2-butyl-7-ethyl-6-methyl-1-(2-methylpropyl)-1H-imidazo[4,5-c]pyridin-4-amine hydrochloride;
2,6-dimethyl-1-(2-methylpropyl)-1H-imidazo[4,5-c]pyridin-4-amine;

2-ethyl-6,7-dimethyl-1-(2-methylpropyl)-1H-imidazo[4,5-c]pyridin-4-amine;

2,6,7-trimethyl-1-(2-phenylethyl)-1H-imidazo[4,5-c]pyridin-4-amine;

2-butyl-6,7-dimethyl-1-(2-phenylethyl)-1H-imidazo[4,5-c]pyridin-4-amine hydrochloride;

6,7-dimethyl-1-(2-phenylethyl)-2-phenylmethyl-1H-imidazo[4,5-c]pyridin-4-amine;

2,6-dimethyl-1-(2-phenylethyl)-1H-imidazo[4,5-c]pyridin-4-amine;

2-ethoxymethyl-6-methyl-1-(2-methylpropyl)-1H-imidazo[4,5-c]pyridin-4-amine;

4-amino-6-methyl-1-(2-methylpropyl)-1H-imidazo[4,5-c]pyridine-2-methanol;

1-butyl-2,6-dimethyl-1H-imidazo[4,5-c]pyridin-4-amine; and 2-butyl-6,7-dimethyl-1-(2-methyl-1-propenyl)-1H-imidazo[4,5-c]pyridin-4-amine hydrochloride.

Compounds of the invention can be prepared according to the Reaction Scheme, wherein $R_1$, $R_2$, $R_6$, and $R_7$ are as defined above. Reaction Scheme I is particularly amenable to the preparation of compounds wherein $R_1$, $R_2$, $R_6$, and $R_7$ are selected from the preferred substituents enumerated above, and R' is alkyl (e.g., lower alkyl, i.e., alkyl of one to about four carbon atoms), perfluoroalkyl (e.g., perfluoro(lower)alkyl such as trifluoromethyl), aryl (e.g., phenyl), alkylaryl (e.g., (lower)alkylphenyl such as 4-methylphenyl), or haloaryl (e.g., halophenyl such as 4-bromophenyl).

Reaction Scheme

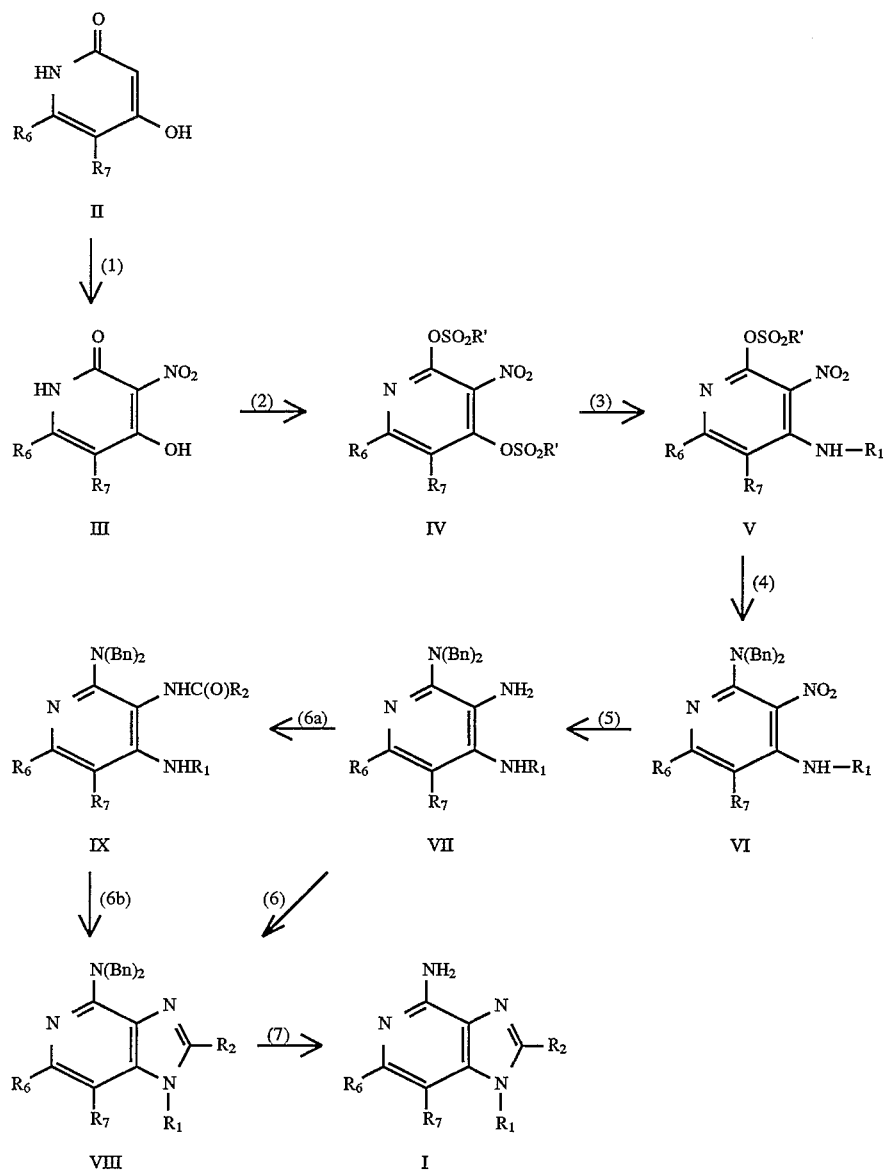

The starting material for use in connection with Reaction Scheme I is a 4-hydroxy-2(1H)-pyridone of Formula II. Certain of these compounds are known. Others can be prepared readily by those skilled in the art, e.g., according to the general methods disclosed in *J. Org. Chem.*, 1941, 6, 54, Tracy et al., *J. Chem. Soc.*, 1962, 3638, Davis et al., *Rel. Trav. Chim.* 1944, 63, 231, Wibout et al., and *Recueil*, 1961, 80, 545, Salemink (incorporated herein by reference).

In step (1) of Reaction Scheme I, a compound of Formula II is nitrated under conventional nitration conditions, such as by heating (e.g., to 100° C.) in the presence of nitric acid, preferably in a solvent such as acetic acid or as disclosed, e.g., in *J. Heterocyclic Chem.*, 1970, 7, 389, Wang. Certain compounds of Formula III can be prepared directly (that is, without the need for nitration of a compound of Formula II) by base catalyzed condensation of a β-aminoester such as ethyl-3-aminocrotonate with a nitromalonate ester such as diethylnitromalonate (according to the general method disclosed, e.g., in *J. Org. Chem*, 1981, 46, 3040, Seeman et al., incorporated herein by reference).

In step (2) 3-nitropyridine-2,4-disulfonate of Formula IV is provided by reacting a compound of Formula III with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobenzenesulfonyl chloride, and p-toluenesulfonyl chloride. Suitable sulfonic anhydrides include those corresponding to the above-mentioned sulfonyl halides. A particularly preferred sulfonic anhydride is trifluoromethanesulfonic anhydride. Sulfonic anhydrides are preferred in view of the fact that the sulfonate anion generated as a byproduct of the reaction is a relatively poor nucleophile and as such does not give rise to undesired side products such as those in which the nitro group has been displaced.

Reaction conditions preferably involve first combining a compound of Formula III with a base, preferably an excess of a tertiary amine base (e.g., a trialkylamine base such as triethylamine) and preferably in an appropriate solvent such as dichloromethane and then adding the sulfonyl halide or the sulfonic anhydride. The addition is preferably carried out in a controlled fashion (e.g., dropwise) and at a reduced temperature (e.g., at about 0° C.). The product can be isolated by conventional methods or it can be carried on without isolation as described below in connection with step (3).

Step (3) of the Reaction Scheme provides the product 3-nitro-4-(substituted)aminopyridine-2-sulfonates. Due to the presence of two sulfonate groups that could in principle be displaced, the reaction affords a mixture of products, which can be readily separated, e.g., by conventional chromatography techniques. The compound of Formula IV is reacted with an amine, preferably in the presence of an excess of a tertiary amine base in a solvent such as dichloromethane. Suitable amines include primary amines affording 4-substituted amino compounds of Formula V wherein the amino substituent is represented by $R_1$. Preferred amines include those amines comprising the groups set forth above in connection with preferred $R_1$ substituents.

The reaction can be carried out by adding the tertiary amine base to the reaction mixture resulting from step (2), cooling to a reduced temperature (e.g., 0° C.) and adding the amine in a controlled fashion (e.g., dropwise). The reaction can also be carried out by adding the amine to a solution of the compound of Formula IV and a tertiary amine base in a solvent such as dichloromethane. As the sulfonate is a relatively facile leaving group the reaction can be run at relatively low temperatures, e.g.; about 0° C., and in relatively non-polar solvents (e.g., toluene) in order to decrease the amount of undesired 2-aminated and 2,4-diaminated side products. It is sometimes necessary or desirable to heat the reaction mixture after the addition in order to complete the reaction. The product can be isolated from the reaction mixture by conventional methods.

In step (4) the compound of Formula V is reacted with a hydrogenolyzable amine to afford a compound of Formula VI. The term "hydrogenolyzable amine" as used herein refers to any amine that is nucleophilic enough to displace the sulfonate group in step (4) and wherein the substituent or substituents can be removed by hydrogenolysis. Such amines are known to those skilled in the art to include arylmethyl amines and di(arylmethyl) amines, i.e., those amines wherein the substituent or substituents are identical or different from one another and with respect to each substituent the amino nitrogen is one carbon removed from an aromatic ring. The term "hydrogenolyzable amino substituent" as used herein refers to the substituent that obtains upon the use of a hydrogenolyzable amine in the reaction of step (4), i.e., a hydrogenolyzable amine absent one hydrogen atom. Primary hydrogenolyzable amines are less preferred, as their use provides an alternative site for cyclization in steps (6), (6a), or (6b) described below. Secondary hydrogenolyzable amines are preferred. Suitable secondary hydrogenolyzable amines include dibenzylamine (i.e., di(phenylmethyl)amine) and substituted derivatives thereof such as di[4-methyl-(phenylmethyl)]amine, di(2-furanylmethyl)amine, and the like. The Reaction Scheme specifically illustrates the process involving dibenzylamine. However, the reaction can be carried out with any suitable hydrogenolyzable amine.

The reaction of step (4) can be carried out by placing the starting material and the hydrogenolyzable amine in an inert solvent such as benzene, toluene, or xylene, and heating at a temperature and for a time sufficient to cause displacement of the sulfonate group by the hydrogenolyzable amine, such temperature and time being readily selected by those skilled in the art. The product can be isolated from the reaction mixture by conventional methods.

In step (5) the nitro group of a compound of Formula VI is reduced to an amino group. Methods for such a reduction are well known to those skilled in the art. A preferred method involves in situ generation of $Ni_2B$ from sodium borohydride and $NiCl_2$ in the presence of methanol. The compound of Formula VI is added to the reducing agent solution to effect reduction of the nitro group. The product can then be isolated by conventional methods.

In step (6) a compound of Formula VII is reacted with a carboxylic acid or an equivalent thereof to afford the cyclized compound of Formula VIII. Suitable equivalents to a carboxylic acid include acid halides, orthoesters, and orthoformates, orthoesters, acid halides, and carboxylic acids other than formic acid giving rise to 2-substituted products wherein the 2-substituent is represented by $R_2$. The reaction can be run in the absence of solvent or preferably in an inert solvent such as xylene or toluene in the presence of a carboxylic acid or equivalent (in the presence of an acid catalyst such as p-toluenesulfonic acid if necessary) with sufficient heating (e.g., at about 80°–150° C. depending on the solvent if any) to drive off any alcohol or water formed as a side product of the reaction.

A compound of Formula VIII can also be prepared in two steps from a compound of Formula VII. The first step, represented by step (6a) of the Reaction Scheme, involves reacting the compound of Formula VII with an acyl halide of the formula $R_2C(O)X$ wherein X is chloro or bromo and $R_2$ is as defined above. The product of Formula IX can be isolated and then cyclized in step (6b) by reacting with methanolic ammonia.

In step (7) the cyclized compound of Formula VIII is hydrogenolyzed to afford the 4-amino compound. Conventional well known catalytic hydrogenation conditions are suitable. Preferred conditions involve heating in formic acid in the presence of Pd(OH)$_2$/C.

Certain compounds of the invention cannot be prepared readily according to the Reaction Scheme due to incompatibility of reagents with certain of the functional groups recited in connection with $R_1$, $R_2$, $R_6$, and $R_7$. Such compounds, however, can be prepared by those skilled in the art using well known methods of functional group protection or manipulation, by appropriate adaptation of the synthetic methods disclosed in U.S. Pat. Nos. 4,988,815 (Andre), or by adaptations of the synthetic methods disclosed in U.S. Pat. Nos. 4,689,338, 5,037,985, and 5,175,296, EP-A 90.301766.3, PCT/US91/06682, PCT/US92/01305, and PCT/US92/07226 (Gerster), the relevant disclosures of each of these being incorporated herein by reference.

The product compound of Formula I can be isolated by the conventional means disclosed in U.S. Pat. No. 4,689,338 (Gerster), such as, for example, removal of the solvent and recrystallization from an appropriate solvent (e.g., N,N-dimethylformamide) or solvent mixture, by dissolution in an appropriate solvent (such as methanol) and re-precipitation by addition of a second solvent in which the compound is insoluble, or by column chromatography.

A compound of Formula I can be used as an immunomodulating agent itself or it can be used in the form of a pharmaceutically acceptable acid-addition salt such as a hydrochloride, dihydrogen sulfate, trihydrogen phosphate, hydrogen nitrate, methanesulfonate or a salt of another pharmaceutically acceptable acid. A pharmaceutically acceptable acid-addition salt of a compound of Formula I can be prepared, generally by reaction of the compound with an equimolar amount of a relatively strong acid, preferably an inorganic acid such as hydrochloric, sulfuric, or phosphoric acid, or an organic acid such as methanesulfonic acid, in a polar solvent. Isolation of the salt is facilitated by the addition of a solvent, such as diethyl ether, in which the salt is insoluble.

A compound of the invention can be formulated for the various routes of administration in a pharmaceutically acceptable vehicle, such as water or polyethylene glycol, along with suitable adjuvants, excipients, and the like. Particular formulations can be readily selected by those skilled in the art. Suitable formulations for topical application include creams, ointments and like formulations known to those skilled in the art (e.g., formulations analogous to those disclosed in commonly assigned copending application 07/845,323, incorporated herein by reference). Parenteral formulations are also suitable (e.g., formulations analogous to those disclosed in EP-A-90.304812.0, incorporated herein by reference).

A pharmaceutical composition of the invention comprises a therapeutically effective amount of an imidazopyridin-4-amine. The amount that constitutes a therapeutically effective amount will depend on the particular compound, the particular formulation, the route of administration, and the intended therapeutic effect. Those skilled in the art can determine a therapeutically effective amount with due consideration of such factors.

A number of compounds of Formula I were tested and found to induce biosynthesis of interferon in human cells. The test methods and results are set forth below. As a result of this immunomodulating activity the compounds exhibit antiviral and antitumor activity. They can therefore be used to control viral infections as well as tumors. For example, a compound of Formula I can be used as an agent to control infections in mammals caused by Type II Herpes simplex virus. Compounds of Formula I can also be used to treat a herpes infection by oral, topical, or intraperitoneal administration. The results below suggest that at least certain compounds of the invention might be useful in treating other diseases such as warts, Hepatitis B and other viral infections, cancer such as basal cell carcinoma, and other neoplastic diseases.

In the following Examples, all reactions were run with stirring under an atmosphere of dry nitrogen unless otherwise indicated. The structures were confirmed by nuclear magnetic resonance spectroscopy. The particular materials and amounts thereof recited in the Examples, as well as other conditions and details, should not be construed to unduly limit the invention.

EXAMPLE 1

6-Methyl-3-nitropyridine-2,4-bis (trifluoromethanesulfonate)

Triethylamine (24.5 mL, 0.176 moles) was added to a mixture of 4-hydroxy-6-methyl-3-nitro-2(1H)-pyridinone (15 g, 0.088 mole) in methylene chloride (700 mL.). The reaction mixture was cooled to 5° C. Trifluoromethanesulfonic anhydride (50 g, 0.176 mole) was slowly added to the reaction mixture while maintaining the temperature below 15° C. After the addition was completed, the reaction mixture was stirred at 5° C. for 15 minutes. The ice bath was removed and the reaction mixture was stirred for an additional 2 hours. The, reaction mixture was diluted with water. The organic phase was separated, dried over magnesium sulfate, filtered through a layer of silica gel then concentrated under a stream of nitrogen to provide 32.4 g of solid. A portion (1.4 g) of this solid was recrystallized from petroleum ether to provide the desired product as a solid, m.p. 50°–52° C. Analysis: Calculated for $C_8H_4F_6N_2O_8S_2$: % C, 22.13; % H, 0.93; % N, 6.45; Found: % C, 22.08; % H, 0.84; % N, 6.49.

EXAMPLE 2

6-Methyl-3-nitro-4-[(phenylethyl)amino)]-2-pyridinyl trifluoromethanesulfonate

Triethylamine (10 mL) was added to a mixture of 6 - m e t h y l - 3 - n i t r o p y r i d i n e - 2 , 4 - b i s (trifluoromethanesulfonate) (31 g, 0.071 moles) in methylene chloride (300 mL). The reaction mixture was cooled in an ice bath. Phenethylamine (9 mL) was diluted with methylene chloride (50 mL) then slowly added to the reaction mixture. After the addition was completed, the reaction mixture was stirred with cooling for about 1 hour then at ambient temperature overnight. The reaction mixture was diluted with additional methylene chloride, washed twice with water, washed twice with aqueous sodium bicarbonate, dried over magnesium sulfate and then concentrated under vacuum to provide an orange liquid. This liquid was eluted through a layer of silica gel with methylene chloride then slurried with petroleum ether to provide 16 g of a yellow solid. A small portion (1 g) of this material was recrystallized twice from cyclohexane to provide the desired product as a solid m.p. 78°–79° C. Analysis: Calculated for $C_{15}H_{14}F_3N_3O_5S$: % C, 44.45; % H, 3.48; % N, 10.37; Found: % C, 44.81; % H, 3.42; % N, 10.28.

EXAMPLE 3

6-Methyl-4-[(2-methylpropyl)amino]-3-nitro-2-pyridinyl trifluoromethanesulfonate Triethylamine (8.34 mL, 0.06 mole) was added to a cooled (0° C.) solution of 4-hydroxy-6-methyl-3-nitro-2

(1H)-pyridinone (5.0 g, 0.03 moles) in methylene chloride (300 mL). Trifluoromethanesulfonic anhydride (10.1 mL, 0.06 moles) was added and the resulting mixture was stirred at 0° C. for about 30 minutes. Isobutylamine (8.94 mL, 0.09 mole) was added and the reaction mixture was stirred for about 30 minutes. The reaction mixture was quenched with water (500 mL,) then extracted with methylene chloride (3×50 mL). The extracts were combined, dried over magnesium sulfate then concentrated under vacuum to provide an orange oil. The oil was purified by silica gel column chromatography eluting with hexane:ethyl acetate (70:30) to provide 3.4 g of the desired product as a yellow solid.

EXAMPLE 4

4-[(2-Hydroxy-2-methylpropyl)amino]-5,6-dimethyl-3-nitro-2-pyridinyl trifluoromethanesulfonate Triethylamine (1.2 mL, 8.69 mmoles) was added to a suspension of 4-hydroxy-5,6-dimethyl-3-nitro-2(1H)-pyridinone (0.8 g, 4.3 mmole) in methylene chloride (25 mL). The resulting solution was cooled in an ice bath. Trifluoromethanesulfonic anhydride (1.46 mL, 8.69 mmole) was added dropwise to the solution. After the addition was complete, the ice bath was removed and the reaction was allowed to warm to ambient temperature over a period of 30 minutes. The reaction mixture was filtered through a layer of silica gel then the silica gel was eluted with additional methylene chloride. The filtrate was concentrated under vacuum to provide 1.6 g (3.57 mmole) of 5,6-dimethyl-3-nitropyridine-2,4-bis(trifluoromethanesulfonate. This material was taken up in methylene chloride (30 mL) then cooled in an ice bath. 2-Hydroxyisobutylamine (0.32 g, 3.57 mmole) and triethylamine (0.5 mL, 3.57 mmole) were added to the cooled solution then the reaction mixture was allowed to warm to ambient temperature. The reaction mixture was diluted with methylene chloride, washed with water, dried over magnesium sulfate and then concentrated under vacuum to provide a yellow oil. The oil was purified by silica gel column chromatography eluting with ethyl acetate-:hexane (25:75) to provide 0.7 g of the desired product as a solid, m.p. 79°–80° C. Analysis: Calculated for $C_{12}H_{16}N_3O_6S$: % C, 37.21; % H, 4.16; % N, 10.85; Found: % C, 37.47; % H, 4.13; % N, 10.89.

EXAMPLES 5–9

Using the general method of Example 3, 4-hydroxy-3-nitro-2(1H)-pyridinones of Formula II were reacted first with trifluoromethanesulfonic anhydride then with an amine of formula $R_1N_2$ to provide the intermediates of Formula IV shown in Table 1.

TABLE 1

| Example Number | Intermediate of Formula II | | Intermediate of Formula IV | | |
|---|---|---|---|---|---|
| | $R_6$ | $R_7$ | $R_6$ | $R_7$ | $R_1$ |
| 5 | methyl | H | methyl | H | n-butyl |
| 6 | methyl | methyl | methyl | methyl | 2-phenylethyl |
| 7 | methyl | methyl | methyl | methyl | 2-methylpropyl |
| 8 | chloro | methyl | chloro | methyl | 2-methylpropyl |
| 9 | chloro | methyl | chloro | methyl | 1,1-dimethylethyl |

EXAMPLE 10

$N^4$-Butyl-6-methyl-3-nitro-$N^2$,$N^2$-bis(phenylmethyl) pyridine-2,4-diamine

Dibenzylamine (1.04 g, 5.28 mmole), triethylamine (0.53 g, 5.28 mmole), 4-butylamino-6-methyl-3-nitro-2-pyridinyl trifluoromethanesulfonate (1.72 g, 5.28 mmole) and toluene (45 mL) were combined and heated at reflux for 18 hours. The reaction mixture was cooled to ambient temperature then filtered through a layer of silica gel. The silica gel was eluted with methylene chloride. The combined organic filtrates were evaporated to provide 2.08 g of an oily semisolid.

EXAMPLES 11–17

Using the general method of Example 10, the intermediates of Formula V shown in Table 2 were prepared by reacting the indicated intermediate of Formula IV with dibenzylamine.

TABLE 2

| Example Number | Intermediate of Formula IV Example | Intermediate of Formula V | | |
|---|---|---|---|---|
| | | $R_6$ | $R_7$ | $R_1$ |
| 11 | 2 | methyl | H | 2-phenylethyl |
| 12 | 3 | methyl | H | 2-methylpropyl |
| 13 | 4 | methyl | methyl | 2-hydroxy-2-methylpropyl |
| 14 | 6 | methyl | methyl | 2-phenylethyl |
| 15 | 7 | methyl | methyl | 2-methylpropyl |
| 16 | 8 | chloro | methyl | 2-methylpropyl |
| 17 | 9 | chloro | methyl | 1,1-dimethylethyl |

EXAMPLE 18

6-Methyl-$N^4$-(2-methylpropyl)-$N^2$,$N^2$-bis(phenylmethyl)pyridine-2,3,4-triamine Sodium borohydride (585 mg, 16 mmole) was added to a solution of nickel (II) chloride hydrate (1.02 g, 4.3 mmole) in methanol (100 mL). The addition caused a black solid to form along with gas evolution. The resulting heterogeneous mixture was stirred at ambient temperature for 30 minutes. A solution containing 6-methyl-$N^4$-(2-methylpropyl)-3-nitro-$N^2$, $N^2$-bis(phenylmethyl)pyridine-2,4-diamine (3.47 g, 8.6 mmole) in methylene chloride (20 mL) was added followed by the addition of sodium borohydride (1.37 g, 36 mmole). The reaction mixture was stirred at ambient temperature for about 30 minutes then eluted through a layer of silica gel with a methanol/methylene chloride mixture. The filtrate was concentrated under vacuum. The resulting residue was partitioned between ethyl acetate and water. The ethyl acetate layer was separated, dried with magnesium sulfate and concentrated under vacuum to provide 2.74 g of the desired product as a green foam.

EXAMPLES 19–25

Using the general method of Example 18, the intermediates of Formula VI shown in Table 3 were prepared by reducing the indicated intermediate of Formula V.

TABLE 3

| Example Number | Intermediate of Formula V Example | Intermediate of Formula VI | | |
|---|---|---|---|---|
| | | $R_6$ | $R_7$ | $R_1$ |
| 19 | 10 | methyl | H | n-butyl |
| 20 | 11 | methyl | H | 2-phenylethyl |
| 21 | 13 | methyl | methyl | 2-hydroxy-2-methylpropyl |
| 22 | 14 | methyl | methyl | 2-phenylethyl |

TABLE 3-continued

| Example Number | Intermediate of Formula V Example | Intermediate of Formula VI | | |
|---|---|---|---|---|
| | | $R_6$ | $R_7$ | $R_1$ |
| 23 | 15 | methyl | methyl | 2-methylpropyl |
| 24 | 16 | chloro | methyl | 2-methylpropyl |
| 25 | 17 | chloro | methyl | 1,1-dimethylethyl |

EXAMPLE 26

$N^3$-Acetyl-6-methyl-$N^4$-(2-phenylethyl)-$N^2$,$N^2$-bis(phenylmethyl)pyridine-2,3,4-triamine Triethylamine (2 mL) was added to a solution of 6-methyl-$N^4$-(2-phenylethyl)-$N^2$,$N^2$-bis(phenylmethyl)-pyridine-2,3,4-triamine (6 g, 14.2 mmole) in methylene chloride (50 mL). Acetyl chloride (1.1 mL, 15.5 mmole) was slowly added to the reaction mixture which was then heated on a steam bath for about 1 hour. The reaction mixture was stirred at ambient temperature overnight then diluted with water and methylene chloride. The organic phase was separated, washed with water, dried over magnesium sulfate and then concentrated under vacuum to provide a light green solid. This solid was slurried with ethyl acetate/hexane then recrystallized from ethyl acetate/hexane to provide 4.1 g of a white solid. A small portion (0.8 g) was purified by silica gel column chromatography to provide the desired compound as a white solid, m.p. 152°–153° C. Analysis: Calculated for $C_{30}H_{32}N_4O$: % C, 77.56; % H, 6.94; % N, 12.06; Found: % C, 77.61; % H, 6.89: % N, 12.05.

EXAMPLES 27–28

Using the general method of Example 26 except that the triethylamine was omitted, the intermediates of Formula VII shown in Table 4 were prepared by reacting the indicated intermediate of Formula VI with an acid chloride of formula $R_2C(O)Cl$.

EXAMPLE 29

2,6-Dimethyl-1-(2-phenylethyl)-$N^4$,$N^4$-bis(phenylmethyl)-1H-imidazo[4,5-c]pyridin-4-amine $N^3$-Acetyl-6-methyl-$N^4$-(2-phenylethyl)-$N^2$,$N^2$-bis(phenylmethyl)pyridine-2,3,4-triamine (3.9 g, 8.39 mmole) was combined with 12 wt % ammonia in methanol (40 mL), placed in a Parr bomb and heated at 150° C. for 5 hours. The resulting solid was collected then purified by silica gel column chromatography eluting with ethyl acetate:hexane (20:80) to provide 2.56 g of the desired product as a solid, m.p. 124°–126° C. Analysis: Calculated for $C_{30}H_{30}N_4$: % C, 80.68; % H, 6.77; % N, 12.55; Found: % C, 80.24; % H, 6.68; % N, 12.42.

EXAMPLES 30–31

Using the general method of Example 29, the intermediates of Formula VIII shown in Table 5 were prepared by cyclizing the indicated intermediate of Formula VII.

TABLE 5

| Example Number | Intermediate of Formula VII Example | Intermediate of Formula VIII | | | |
|---|---|---|---|---|---|
| | | $R_6$ | $R_7$ | $R_1$ | $R_2$ |
| 30 | 27 | methyl | H | 2-methylpropyl | methyl |
| 31 | 28 | methyl | methyl | 2-hydroxy-2-methylpropyl | ethoxymethyl |

EXAMPLE 32

6-Chloro-2,7-dimethyl-1-(1,1-dimethylethyl)-$N^4$,$N^4$-bis(phenylmethyl)-1H-imidazo[4,5-c]pyridin-4-amine 6-Chloro-5-methyl-$N^4$-(1,1-dimethylethyl)-$N^2$,$N^2$-bis(phenylmethyl)pyridine-2,3,4-triamine was combined with an excess of triethyl orthoacetate and heated first on a steam bath for about 16 hours and then in an oil bath at 130° C. for 2 hours. The excess triethyl orthoacetate was distilled off under vacuum. The resulting residue was diluted with methylene chloride, washed with water and sodium bicarbonate solution, dried over magnesium sulfate then filtered through a layer of silica gel eluting with additional methylene chloride. The filtrate was concentrated under vacuum to provide a mixture which was carried on to the next step.

EXAMPLE 33

6-Chloro-2,7-dimethyl-$N^4$,$N^4$-bis(phenylmethyl)-1H-imidazo[4,5-c]pyridin-4-amine The material from Example 32 was diluted with toluene then combined with phosphorous oxychloride and heated at reflux overnight. The reaction mixture was concentrated

TABLE 4

| Example Number | Intermediate of Formula VI Example | Intermediate of Formula VII | | | |
|---|---|---|---|---|---|
| | | $R_6$ | $R_7$ | $R_1$ | $R_2$ |
| 27 | 18 | methyl | H | 2-methylpropyl | methyl |
| 28 | 21 | methyl | methyl | 2-hydroxy-2-methylpropyl | ethoxymethyl | under vacuum. The residue was diluted with water, basified with ammonium hydroxide then extracted several times with methylene chloride. The methylene chloride extracts were combined, dried over magnesium sulfate then concentrated under vacuum. The residue was purified by silica gel column chromatography eluting with 10–40% ethyl acetate in hexane to provide the desired product.

EXAMPLE 34

6-Chloro-1-(2-ethoxyethyl)-2,7-dimethyl-$N^4,N^4$-bis (phenylmethyl)-1H-imidazo[4,5-c]pyridin-4-amine Sodium iodide (1.5 g) and potassium carbonate (1 g) were added to a solution of 6-chloro-2,7-dimethyl-$N^4,N^4$-bis (phenylmethyl)-1H-imidazo[4,5-c]pyridin-4-amine (1.0 g, bonate solution, dried over magnesium sulfate then concentrated under vacuum to provide an oil. The oil was purified by silica gel column chromatography eluting with 5–10% ethyl acetate in hexane to provide 1.8 g of the desired product as a white solid, m.p. 139°–141° C. Analysis: Calculated for $C_{37}H_{36}N^4$: % C, 82.80; % H, 6.76; % N, 10.44; Found: % C, 82.86; % H, 6.78; % N, 10.36.

EXAMPLES 37–43

Using the general method of Example 36, the intermediates of Formula VIII shown in Table 6 were prepared by reacting the indicated intermediate of Formula VI with an acid chloride of formula $R_2C(O)Cl$.

TABLE 6

| Example Number | Intermediate of Formula VI Example | Intermediate of Formula VIII | | | |
|---|---|---|---|---|---|
| | | $R_6$ | $R_7$ | $R_1$ | $R_2$ |
| 37 | 18 | methyl | H | 2-methylpropyl | phenylmethoxymethyl |
| 38 | 21 | methyl | methyl | 2-hydroxy-2-methylpropyl | methyl |
| 39 | 21 | methyl | methyl | 2-hydroxy-2-methylpropyl | n-butyl |
| 40 | 22 | methyl | methyl | 2-phenylethyl | methyl |
| 41 | 22 | methyl | methyl | 2-phenylethyl | n-butyl |
| 42 | 23 | methyl | methyl | 2-methylpropyl | methyl |
| 43 | 44 | chloro | methyl | 2-methylpropyl | methyl |

2.7 mmole) in acetone (250 mL). 2-Bromoethyl ethyl ether (0.5 mL, 4.4 mmole) was added and the reaction mixture was heated at reflux overnight. The reaction mixture was filtered and the filtrate concentrated under vacuum. The residue was partitioned between methylene chloride and water. The methylene chloride phase was separated, dried with magnesium sulfate and concentrated under vacuum. The residue was purified by silica gel column chromatography eluting with 10–30% ethyl acetate in hexane to provide 0.7 g of the desired product.

EXAMPLE 35

1-n-Butyl-2,6-dimethyl-$N^4,N^4$-bis(phenylmethyl)-1H-imidazo[4,5-c]pyridin-4-amine $N^4$-n-Butyl-6-methyl-$N^2,N^2$-bis(phenylmethyl)pyridine-2,3,4-triamine (0.65 g, 1.7 mmole) was combined with toluene (10 mL) and acetyl chloride (0.12 mL, 1.7 mmole) and stirred at ambient temperature for 15 minutes. Phosphorous oxychloride (0.31 mL) was added and the reaction mixture was heated at reflux overnight. The reaction mixture was evaporated. The residue was purified by silica gel column chromatography eluting with hexane:ethyl acetate (70:30) to provide 0.18 g of the desired product.

EXAMPLE 36

6,7-Dimethyl-1-(2-phenylethyl)-2,$N^4,N^4$-tris (phenylmethyl)-1H-imidazo[4,5-c]pyridin-4-amine Phenylacetyl chloride (0.6 mL, 4.5 mmole) was added to a solution of 5,6-dimethyl-$N^4$-(2-phenylethyl)-$N^2,N^2$-bis (phenylmethyl)pyridine-2,3,4-triamine (1.96 g, 4.5 mmole) in methylene chloride (100 mL) and the resulting mixture was stirred at ambient temperature overnight. A catalytic amount of p-toluenesulfonic acid was added and stirring was continued at ambient temperature over the weekend. The reaction mixture was washed with saturated sodium bicar-

EXAMPLE 44

2-Ethyl-6,7-dimethyl-1-(2-methylpropyl)-$N^4,N^4$-bis (phenylmethyl)-1H-imidazo[4,5-c]pyridin-4-amine Butyllithium (0.5 mL of 2.5M in hexanes) was added to a cooled (−78° C.) solution of 2,6,7-trimethyl-1-(2-methylpropyl)-$N^4,N^4$-bis(phenylmethyl)-1H-imidazo[4,5-c] pyridin-4-amine (0.5 g, 1.2 mmole) in tetrahydrofuran (30 mL). The reaction mixture was allowed to warm to −10° C. then it was cooled to −78° C. and combined with methyl iodide (0.23 mL, 3.6 mole). The reaction mixture was allowed to warm to ambient temperature then diluted with water and diethyl ether. The ether layer was separated, washed with ammonium chloride solution, dried over magnesium sulfate and then concentrated to provide 0.5 g of the desired product.

EXAMPLE 45

2,6-Dimethyl-1-(2-phenylethyl)-1H-imidazo[4,5-c] pyridin-4-amine

Palladium hydroxide on carbon (0.5 g, Pearlman's catalyst) was added to a mixture of 2,6-dimethyl-1-(2-phenylethyl)-$N^4,N^4$-bis(phenylmethyl)-1H-imidazo[4,5-c] pyridin-4-amine (2.3 g, 5.15 mmole) in formic acid (10 mL). The reaction mixture was heated at reflux overnight. An additional 0.5 g of catalyst was added and refluxing was continued overnight. The reaction mixture was neutralized with saturated sodium bicarbonate solution, diluted with methanol then filtered through a layer of celite to remove the catalyst. The celite layer was flushed with methylene chloride and methanol. The filtrates were combined and concentrated under vacuum to provide a mixture of water and a solid. This mixture was extracted with methylene chloride. The extract was washed with water, dried over magnesium sulfate and concentrated under vacuum to provide 1.2 g of a tan solid. This solid was recrystallized from ethanol to provide 0.24 g of the desired product as a solid, m.p. 185°–187° C. Analysis: Calculated for $C_{16}H_{18}N_4$: % C, 72.15; % H, 6.81; % N, 21.04; Found: % C, 71.51; % H, 6.88; % N, 20.61.

EXAMPLES 46–56

Using the general method of Example 45, the products of Formula I shown in Table 7 were prepared by hydrogenolizing the indicated intermediate of Formula VIII. The melting points and elemental analyses are shown in Table 8.

129°–130° C. Analysis: Calculated for: $C_{12}H_{18}N_4O+\frac{1}{4}H_2O$: % C, 60.35; % H, 7.81; % N, 23.46; Found: % C, 60.64; % H, 7.50; N, 23.39.

EXAMPLE 58

2,7-Dimethyl-1-(2-methylpropyl)-1H-imidazo[4,5-c]pyridin-4-amine

Using the general method of Example 57, 6-chloro-2,7-dimethyl-1-(2-methylpropyl)-$N^4,N^4$-bis(phenylmethyl)-1H-imidazo[4,5-c]pyridin-4-amine (1 g, 2.3 mmole) was hydrogenolized to provide 0.07 g of the desired product as a solid,

TABLE 7

| Example Number | Intermediate of Formula VIII Example | Product of Formula I | | | |
|---|---|---|---|---|---|
| | | $R_6$ | $R_7$ | $R_1$ | $R_2$ |
| 46 | 30 | methyl | H | 2-methylpropyl | methyl |
| 47 | 31 | methyl | methyl | 2-hydroxy-2-methylpropyl | ethoxymethyl |
| 48 | 35 | methyl | H | n-butyl | methyl |
| 49 | 36 | methyl | methyl | 2-phenylethyl | phenylmethyl |
| 50 | 37 | methyl | H | 2-methylpropyl | hydroxymethyl |
| 51 | 38 | methyl | methyl | 2-hydroxy-2-methylpropyl | methyl |
| 52 | 39 | methyl | methyl | 2-hydroxy-2-methylpropyl | n-butyl |
| 53 | 40 | methyl | methyl | 2-phenylethyl | methyl |
| 54 | 41 | methyl | methyl | 2-phenylethyl | n-butyl |
| 55 | 42 | methyl | methyl | 2-methylpropyl | methyl |
| 56 | 44 | methyl | methyl | 2-methylpropyl | ethyl |

TABLE 8

| Example Number | m.p. (°C.) | Formula | Elemental Analysis | | | | | |
|---|---|---|---|---|---|---|---|---|
| | | | Calculated | | | Found | | |
| | | | % C | % H | % N | % C | % H | % N |
| 46 | 153–155 | $C_{12}H_{18}N_4 + 0.15 H_2O$ | 65.21 | 8.25 | 25.35 | 65.38 | 8.41 | 25.37 |
| 47 | 178–181 | $C_{15}H_{24}N_4O_2$ | 60.68 | 8.32 | 18.87 | 60.55 | 8.13 | 19.11 |
| 48 | 130–132 | $C_{12}H_{18}N_4 + 0.2 H_2O$ | 64.95 | 8.36 | 25.25 | 65.01 | 8.10 | 24.9 |
| 49 | 170–173 | $C_{23}H_{24}N_4 + 0.5 H_2O$ | 75.59 | 6.89 | 15.33 | 75.56 | 6.99 | 15.36 |
| 50 | 180–181 | $C_{12}H_{18}N_4O + 0.33 H_2O$ | 59.99 | 7.83 | 23.32 | 59.87 | 7.7 | 23.39 |
| 51 | 249–250 | $C_{13}H_{20}N_4O$ | 62.88 | 8.12 | 22.56 | 62.67 | 8.02 | 22.19 |
| 52 | 167–170 | $C_{16}H_{26}N_4O + 0.75 H_2O$ | 63.07 | 9.10 | 18.39 | 63.40 | 8.75 | 18.33 |
| 53 | 142–145 | $C_{17}H_{20}N_4 + 0.5 H_2O$ | 70.56 | 7.31 | 19.36 | 70.90 | 7.38 | 19.43 |
| 54 | 134–135 | $C_{20}H_{26}N_4 + 0.2 H_2O$ | 73.67 | 8.16 | 17.18 | 73.92 | 8.21 | 17.32 |
| 55 | 157–159 | $C_{13}H_{20}N_4 + 0.2 CH_2Cl_2$ | 63.59 | 8.25 | 22.47 | 63.37 | 8.18 | 22.27 |
| 56 | 163–165 | $C_{14}H_{22}N_4$ | 68.26 | 9.00 | 22.74 | 68.36 | 9.03 | 22.73 |

EXAMPLE 57

1-(2-Ethoxyethyl)-2,7-dimethyl-1H-imidazo[4,5-c]pyridin-4-amine

6-Chloro-1-(2-ethoxyethyl)-2,7-dimethyl-$N^4,N^4$-bis(phenylmethyl)-1H-imidazo[4,5-c]pyridin-4-amine (0.7 g, 1.56 mmole) was taken up in methanol saturated with anhydrous hydrochloric acid (100 mL), combined with palladium hydroxide on carbon and then hydrogenated on a Paar apparatus for four hours. The reaction mixture was filtered to remove the catalyst then concentrated under vacuum. The residue was partitioned between methylene chloride/water/sodium bicarbonate. The methylene chloride layer was separated, dried over magnesium sulfate then concentrated under vacuum to provide an off white solid. This material was recrystallized from ethyl acetate/hexane to provide 0.18 g of the desired product as a solid, m.p. 178°–180° C. Analysis: Calculated for $C_{12}H_{18}N_4$: % C, 66.02; % H, 8.31; % N, 25.66; Found: % C, 65.58; % H, 8.34; % N, 25.30.

EXAMPLE 59

6-Methyl-1-(2-methylpropyl)-2-morpholinomethyl-1H-imidazo[4,5-c]pyridin-4-amine

Part A

6-Methyl-$N^4$-(2-methylpropyl)-$N^2,N^2$-bis(phenylmethyl)pyridine-2,3,4-triamine (2.27 g, 6.1 mmole), ethoxyacetyl chloride (0.74 g, 6.1 mmole) and acetonitrile (100 mL) were combined and stirred at ambient temperature for about 15 minutes to provide a heterogeneous reaction mixture. p-Toluenesulfonic acid (0.1 g) was added and the reaction mixture was heated at reflux for 48 hours. The reaction mixture was cooled to ambient temperature, concentrated under vacuum and then partitioned between methylene chloride and 10% ammonium hydroxide. The organic phase was dried over magnesium sulfate then concentrated to provide 2.8 g of an oil. The oil was dissolved in toluene (100 mL), combined with phosphorus oxychloride (1 mL) and then heated at reflux for 48 hours. The reaction mixture was cooled to ambient temperature, concentrated and then partitioned between methylene chloride and 10% ammonium hydroxide. The organic phase was dried over magnesium sulfate then concentrated to provide a yellow oil. Analysis of the nuclear magnetic resonance spectrum of this material indicated that it contained 2-chloromethyl-6-methyl-1-(2-methylpropyl)-$N^4$,$N^4$-bis(phenylmethyl)-1H-imidazo[4,5-c]pyridin-4-amine and 2-ethoxymethyl-6-methyl-1-(2-methylpropyl)-$N^4$,$N^4$-bis(phenylmethyl)-1H-imidazo[4,5-c]pyridin-4-amine.

Part B

The mixture from Part A was dissolved in methylene chloride (5 mL) then combined with morpholine (2 mL) and stirred at ambient temperature for 48 hours. The reaction mixture was quenched with saturated sodium bicarbonate solution then partitioned between methylene chloride and water. The organic phase was dried over magnesium sulfate then concentrated to provide 1.2 g of an oil. This oil was chromatographed (silica gel; 80:20 hexane:ethyl acetate) to provide 0.6 g of 6-methyl-1-(2-methylpropyl)-2-morpholinomethyl-$N^4$,$N^4$-bis(phenylmethyl)-1H-imidazo[4,5-c]pyridin-4-amine and 0.4 g of 2-ethoxymethyl-6-methyl-1-(2-methylpropyl)-$N^4$,$N^4$-bis(phenylmethyl)-1H-imidazo[4,5-c]pyridin-4-amine.

Part C

Using the general method of Example 45, 6-methyl-1-(2-methylpropyl)-2-morpholinomethyl-$N^4$,$N^4$-bis(phenylmethyl)-1H-imidazo[4,5-c]pyridin-4-amine (0.6 g, Part B) was hydrogenolized to provide 0.31 g of the desired product as a white solid, m.p. 188°–190° C. Analysis: Calculated for $C_{16}H_{25}N_5O+\frac{1}{3}H_2O$: % C, 62.11; % H, 8.36; % N, 22.63; Found: % C, 62.19; % H, 8.18; % N, 22.62.

EXAMPLE 60

2-Ethoxymethyl-6-methyl-1-(2-methylpropyl)-1H-imidazo[4,5-c]pyridin-4-amine

Using the general method of Example 45, 2-ethoxymethyl-6-methyl-1-(2-methylpropyl)-$N^4$,$N^4$-bis(phenylmethyl)-1H-imidazo[4,5-c]pyridin-4-amine (0.4 g, Example 73, Part B) was hydrogenolized to provide 0.08 g of the desired product as an off white solid, m.p. 72°–74° C. Analysis: Calculated for $C_{14}H_{22}O+\frac{1}{2}CH_3OH$: % C, 62.56; % H, 8.69; % N, 20.13; Found: % C, 62.93; % H, 8.37; % N, 19.8.

EXAMPLE 61

2-Butyl-6,7-dimethyl-1-(2-methyl-1-propenyl)-1H-imidazo[4,5-c]pyridin-4-amine hydrochloride 4-Amino-2-butyl-α,α,6,7-tetramethyl-1H-imidazo[4,5-c]pyridine-1-ethanol (about 200 mg) was combined with concentrated hydrobromic acid (50 mL,) and heated at reflux overnight. The reaction mixture was concentrated under vacuum. The residue was taken up in methanol then diluted with ether. The resulting precipitate was collected then partitioned between methylene chloride and 10% sodium hydroxide. The organic layer was separated, dried over magnesium sulfate then concentrated to provide an oil. The oil was taken up in methanol then combined with 0.05 mL of concentrated hydrochloric acid followed by dilution with ether. The resulting precipitate was collected, rinsed with ether and dried to provide 60 mg of the desired product as a white solid, m.p. 205° C. (dec.). Analysis: Calculated for $C_{16}H_{24}N_4+1.6$ HCl: % C, 58.10; % H, 7.80; % N, 16.94; Found: % C, 57.95; % H, 7.87; % N, 16.89.

EXAMPLE 62

2-Butyl-7-ethyl-6-methyl-1-(2-methylpropyl)-1H-imidazo[4,5-c]pyridin-4-amine Hydrochloride Part A Using the general method of Example 3, 5-ethyl-4-hydroxy-6-methyl-3-nitro-2(1H)-pyridinone (1.0 g, 5 mmole) was reacted first with trifluoromethanesulfonic anhydride (1.7 mL, 10 mmole) and then with isobutylamine (0.55 mL, 5.5 mole) to provide 1.0 g of 5-ethyl-6-methyl-4-[(2-methylpropyl)amino]-3-nitro-2-pyridinyl trifluoromethanesulfonate.

Part B

Using the general method of Example 10, the material from Part A was reacted with dibenzylamine (0.52 mL) to provide 1.0 g of 5-ethyl-6-methyl-$N^4$-(2-methylpropyl)-3-nitro-$N^2$,$N^2$-bis(phenylmethyl)pyridine-2,4-diamine.

Part C

Using the general method of Example 18, the material from Part B was reduced to provide 0.85 g of 5-ethyl-6-methyl-$N^4$-(2-methylpropyl)-$N^2$,$N^2$-bis(phenylmethyl)pyridine-2,3,4-triamine as a light brown oil.

Part D

The material from Part C was dissolved in acetonitrile (20 mL) then combined with valeryl chloride (0.28 mL) and stirred first at ambient temperature overnight, then at reflux for 3 hours and then at ambient temperature over the weekend. The reaction mixture was concentrated under vacuum. The residue was taken up in methylene chloride, washed with 10% sodium hydroxide, dried over magnesium sulfate then filtered through a layer of silica gel eluting with 30% ethyl acetate in hexane. The filtrate was concentrated under vacuum to provide 0.65 g of 2-butyl-7-ethyl-6-methyl-1-(2-methylpropyl)-$N^4$,$N^4$-bis(phenylmethyl)-1H-imidazo[4,5-c]pyridin-4-amine as a golden oil.

Part E

The material from Part D was dissolved in formic acid (20 mL), combined with palladium hydroxide on carbon (0.5 g, Pearlman's catalyst) then heated at reflux. The reaction mixture was filtered through a layer of celite eluting with methanol to remove the catalyst then concentrated under vacuum. The residue was partitioned between methylene chloride and aqueous sodium bicarbonate. The methylene chloride layer was dried over magnesium sulfate then concentrated under vacuum. The residue was recrystallized from ethyl acetate/hexane to provide product which by nuclear magnetic resonance spectroscopy contained some formate salt. This material was taken up in methanol, combined with 10% sodium hydroxide then heated on a steam bath for 1 hour. The mixture was concentrated to remove the methanol then extracted with methylene chloride. The methylene chloride extract was dried with magnesium sulfate then concentrated under vacuum to provide an oily residue. This residue was taken up in diethyl ether then combined with 1 equivalent of 1M hydrochloric acid in ether. The resulting precipitate was collected by filtration and dried to provide 0.15 g of the desired product as a solid, m.p. 217°–219° C. Analysis: Calculated for $C_{17}H_{28}N_4$ HCl: % C, 62.85; % H, 9.00; % N, 17.24; Found: % C, 62.39; % H, 8.70; % N, 16.76.

INTERFERON (α) INDUCTION IN HUMAN CELLS

An in vitro human blood cell system was used to assess interferon induction by compounds of the invention. Activity is based on the measurement of interferon secreted into culture media. Interferon is measured by bioassay.

Blood Cell Preparation for Culture

Whole blood is collected by venipuncture into EDTA vacutainer tubes. Peripheral blood mononuclear cells (PBM's) are separated from whole blood by using either LeucoPREP™ Brand Cell Separation Tubes (available from Becton Dickinson) or Ficoll-Paque® solution (available from Pharmacia LKB Biotechnology Inc, Piscataway, N.J.). The PBM's are suspended at $1\times10^6$/mL in RPMI 1640 media (available from GIBCO, Grand Island, N.Y.) containing 25 mM HEPES (N-2-hydroxyethylpiperazine-N'-2-ethanesulfonic acid) and L-glutamine (1% penicillin-streptomycin solution added) with 10% heat inactivated (56° C. for 30 minutes) autologous serum added. 200 µL portions of PBM suspension are added to 96 well (flat bottom) MicroTest III sterile tissue culture plates.

Compound Preparation

The compounds are solubilized in ethanol, dimethyl sulfoxide or tissue culture water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. Compounds are initially tested in a concentration range of from about 0.1 µg/mL to about 5 µg/mL. Compounds which show induction at a concentration of 0.5 µg/mL are then tested in a wider concentration range.

Incubation

The solution of test compound is added in a volume (less than or equal to 50 µL) to the wells containing 200 µL of PBM's in media. Solvent and/or media is added to control wells (wells with no test compound) and as needed to adjust the final volume of each well to 250 µL. The plates are covered with plastic lids, vortexed gently and then incubated for 48 hours at 37° C. with a 5% carbon dioxide atmosphere.

Separation

Following incubation, the plates are covered with parafilm and then centrifuged at 1000 rpm for 10 to 15 minutes at 4° C. in a Damon IEC Model CRU-5000 centrifuge. Media (about 200 µL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates" Biotechniques, June/July; 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as alpha reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus. Results are shown in the table below wherein the absence of an entry indicates that the compound was not tested at that particular concentration.

Interferon (α) Induction in Human Cells

| Compound of Example Number | α Reference units/mL Dose Concentration (µg/mL) | | | | | | | | |
|---|---|---|---|---|---|---|---|---|---|
| | 0.001 | 0.005 | 0.01 | 0.05 | 0.1 | 0.5 | 1.0 | 5.0 | 10 | 25 |
| 45 | | | 0 | 3 | 0 | 1 | 3 | 93 | | |
| 46 | | | 4 | 4 | 4 | 4 | 4 | 50 | | |
| 47 | 8 | 8 | 1 | 190 | 190 | 65 | 61 | 49 | | |
| 48 | | | 1 | 1 | 1 | 1 | 1 | 110 | 100 | 19 |
| 49 | | | 1 | 1 | 10 | 930 | 830 | 70 | | |
| 50 | | | 1 | 1 | | 1 | 1 | 9 | 37 | 210 |
| 51 | | | 1 | 1 | 23 | 520 | 520 | 100 | | |
| 52 | 1 | 82 | 160 | 45 | 150 | 150 | 150 | 320 | | |
| 53 | | | 1 | 230 | 780 | 280 | 87 | 70 | | |
| 54 | | | 1 | 260 | 880 | 70 | 70 | 70 | | |
| 55 | | | 1 | 8 | 130 | 340 | 210 | 110 | | |
| 56 | | | 4 | 680 | 1100 | 130 | 150 | 200 | | |
| 57 | | | 4 | 4 | 4 | 4 | 2 | 320 | | |
| 58 | | | 3 | 3 | 7 | 790 | 1200 | 150 | | |
| 59 | | | 1 | 1 | 1 | 1 | 1 | 1 | 1 | 1 |
| 60 | | | 1 | 1 | 1 | 10 | 230 | 170 | 61 | 61 |
| 61 | | | 3 | 684 | 395 | 684 | 300 | 520 | | |
| 62 | | | 107 | 42 | 62 | 81 | 81 | 81 | | |

INDIRECT IN-VITRO ANTIVIRAL ACTIVITY

The test method described below demonstrates the ability of compounds of the invention to inhibit the progress of viral infection.

Whole blood is collected by venipuncture into EDTA vacutainer tubes. Peripheral blood mononuclear cells (PBM's) are isolated using Ficoll-Paque® solution (available from Pharmacia LKB Biotechnology Inc., Piscataway, N.J.). The PBM's are washed with phosphate buffer saline then diluted with RPMI 1640 medium (available from GIBCO, Grand Island, N.Y.) and 10% fetal bovine serum to obtain a final concentration of $2.5\times10^6$ cells/mL. One mL portions of PBM's in medium are placed in 15 mL polypropylene tubes. The test compound is dissolved in dimethyl sulfoxide then diluted with RPMI 1640 medium. The solution of test compound is added to the tubes containing the PBM's to give final concentrations ranging from 0.1 μg/mL to 1.0 μg/mL. Control tubes do not receive any test compound. The tubes are then incubated for 24 hours at 37° C. with a 5% carbon dioxide atmosphere. Following incubation the tubes are centrifuged at 400 xg for 5 minutes. The supernatant is removed. The PBM's are brought up in 100 μL of RPMI 1640 medium and then infected with a 100 μL containing $10^5$ tissue culture 50% infectious doses of vesicular stomatitis virus (VSV). The tubes are incubated for 30 minutes at 37° C. to allow virus adsorption. One mL of RPMI 1640 medium is added to each tube and the tubes are incubated for 48 hours at 37° C. The tubes are frozen then thawed to lyse the cells. The tubes are centrifuged at 400 xg for 5 minutes to remove cellular debris then the supernatant is assayed by serial tenfold dilutions on Vero cells in 96 well microtiter plates. The infected cells are incubated for 24 hours at 37° C. before quantifying for viral cytopathic effect. The viral cytopathic effect is quantified by staining with 0.05% crystal violet. Results are presented as VSV inhibition, defined as the $\log_{10}$ (control VSV yield/experimental VSV yield). Control tubes have a value of 0. Results are shown in the table below.

| Compound of Example Number | In-vitro Antiviral Activity VSV Yield Inhibition Dose Concentration (μg/mL) | | |
|---|---|---|---|
| | 0.1 | 0.5 | 1.0 |
| 45 | 0.0 | 0.0 | 0.0 |
| 47 | 5.0 | 5.0 | 6.0 |
| 41 | 0.0 | 3.0 | 4.0 |
| 50 | 0.0 | 0.0 | 0.0 |
| 53 | 5.0 | 7.0 | 6.0 |
| 54 | 4.0 | 5.0 | 5.0 |
| 56 | 5.0 | 5.0 | 6.0 |
| 57 | 0.0 | 0.0 | 2.0 |
| 59 | 0.0 | 0.0 | 0.0 |
| 60 | 0.0 | 2.0 | 6.0 |
| 61 | 5.0 | 5.0 | 6.0 |

The claimed invention is:
1. A compound of the formula

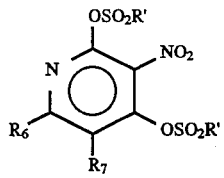

wherein $R_6$ and $R_7$ are independently selected from the group consisting of hydrogen and alkyl of one to about five carbon atoms, with the proviso that $R_6$ and $R_7$ taken together contain no more than six carbon atoms, and with the further proviso that when $R_7$ is hydrogen then $R_6$ is other than hydrogen; and R' is alkyl, perfluoroalkyl, alkylaryl, or haloaryl.

2. A compound of the formula

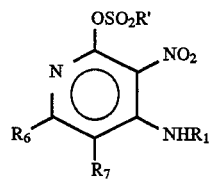

wherein $R_1$ is selected from the group consisting of hydrogen; $CHR_xR_y$ wherein $R_x$ is hydrogen and $R_y$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and $-CH=CR_zR_z$ wherein each $R_z$ is independently straight chain, branched chain, or cyclic alkyl of one to about six carbon atoms;

$R_6$ and $R_7$ are independently selected from the group consisting of hydrogen and alkyl of one to about five carbon atoms, with the proviso that $R_6$ and $R_7$ taken together contain no more than six carbon atoms, and with the further proviso that when $R_7$ is hydrogen then $R_6$ is other than hydrogen; and R' is alkyl, perfluoroalkyl, alkylaryl, or haloaryl.

3. A compound of the formula

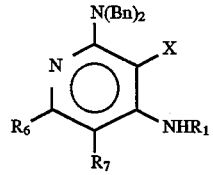

wherein X is $-NO_2$ or $-NH_2$;

$R_6$ and $R_7$ are independently selected from the group consisting of hydrogen and alkyl of one to about five carbon atoms, with the proviso that $R_6$ and $R_7$ taken together contain no more than six carbon atoms, and with the further proviso that when $R_7$ is hydrogen then $R_6$ is other than hydrogen;

$R_1$ is selected from the group consisting of hydrogen; $CHR_xR_y$ wherein $R_x$ is hydrogen and $R_y$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and $-CH=CR_zR_z$ wherein each $R_z$ is independently straight chain, branched chain, or cyclic alkyl of one to about six carbon atoms; and Bn is a hydrogenolyzable amino substituent.

* * * * *